United States Patent [19]

Monaghan

[11] Patent Number: 5,278,320
[45] Date of Patent: Jan. 11, 1994

[54] CHOLESTEROL LOWERING COMPOUNDS PRODUCED BY DIRECTED BIOSYNTHESIS

[75] Inventor: Richard L. Monaghan, Somerset, N.J.

[73] Assignee: Merck & Co., Inc., Rahway, N.J.

[21] Appl. No.: 943,661

[22] Filed: Sep. 11, 1992

[51] Int. Cl.$^5$ .................. C07D 405/12; C07D 407/12
[52] U.S. Cl. ...................... 549/60; 546/270; 548/311.7; 548/463; 549/363
[58] Field of Search .................. 549/60, 363; 546/270; 514/444, 452, 338; 548/311.7, 463

[56] References Cited

U.S. PATENT DOCUMENTS 5,053,425 10/1991 Bartizal et al. .................. 514/452
5,096,923 3/1992 Bergstrom et al. .................. 514/452

FOREIGN PATENT DOCUMENTS

| 0494622 | 7/1992 | European Pat. Off. |
| 0503520 | 9/1992 | European Pat. Off. |
| WO92/12156 | 7/1992 | World Int. Prop. O. |
| WO92/12157 | 7/1992 | World Int. Prop. O. |
| WO92/12158 | 7/1992 | World Int. Prop. O. |
| WO92/12159 | 7/1992 | World Int. Prop. O. |
| WO92/12160 | 7/1992 | World Int. Prop. O. |

OTHER PUBLICATIONS

Kobel and Traber, European Journal App. Microbiol. Biotechnol. 14: 237–240 (1982).
Hensens et al., J. Antibiotics, 45: 133–135 (1992).

*Primary Examiner*—Richard L. Raymond
*Attorney, Agent, or Firm*—Catherine A. Dolan; Melvin Winokur; Paul D. Matukaitis

[57] ABSTRACT

Compounds of Structural Formula (I)

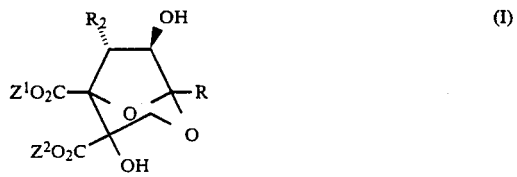

are produced by chemical modification of directed biosynthesis products. These compounds are squalene synthetase inhibitors and thus useful as cholesterol lowering agents, antifungal agents and cancer treatment agents.

8 Claims, No Drawings

CHOLESTEROL LOWERING COMPOUNDS PRODUCED BY DIRECTED BIOSYNTHESIS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR ® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorus containing inhibitors of squalene synthetase have been isolated as natural products. These natural product inhibitors are described in U.S. Pat. Nos. 5,053,425; 5,055,487 and 5,026,554.

U.S. Pat. No. 5,053,425 discloses a zaragozic acid compound of structure

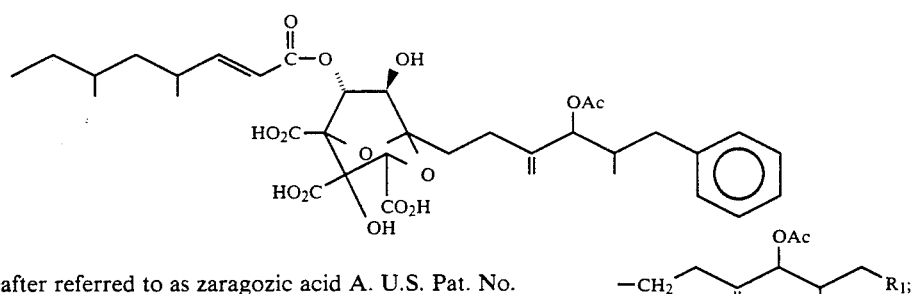

hereafter referred to as zaragozic acid A. U.S. Pat. No. 5,026,554 discloses a zaragozic acid compound of structure

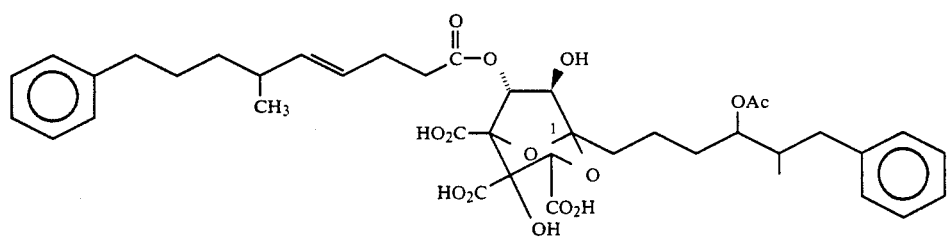

hereafter referred to as Zaragozic acid C.

DETAILED DESCRIPTION OF THE INVENTION

The present invention is directed to compounds of structural formula (I):

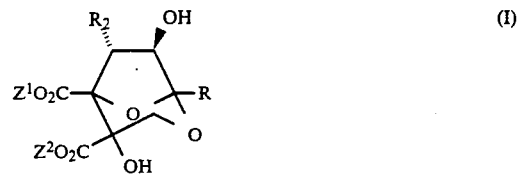

(I)

wherein
R is selected from

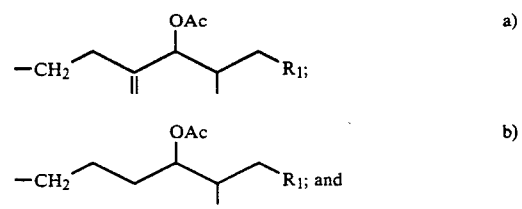

a)

b)

$R_2$ is selected from

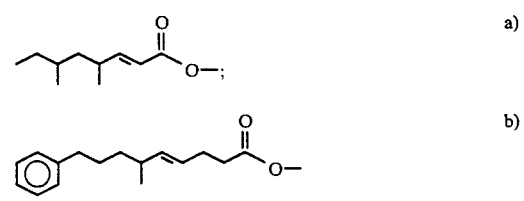

a)

b)

Provided that when R is

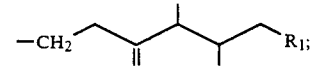

a)

then $R_2$ is

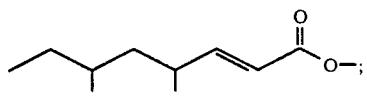

and when R is

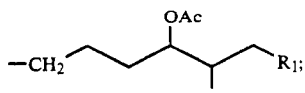

then $R_2$ is

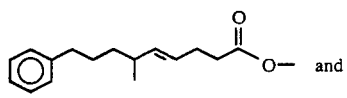

$R_1$ is selected from (a)

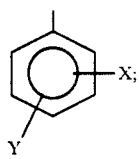

(b)

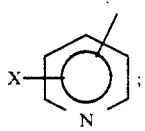

(c)

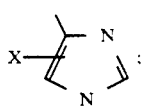

(d)

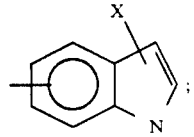

(e)

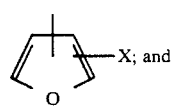

(f)

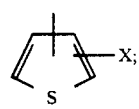

wherein X and Y are selected from the group consisting of:
(a) H;
(b) halogen (F, Cl, Br, I);
(c) OH; and
(d) $CH_3$; provided that when $R_1$ is phenyl, X and Y are not both hydrogen;

and wherein $Z^1$ and $Z^2$, are each independently selected from the group consisting of
(a) H;
(b) $C_{1-5}$alkyl;
(c) $C_{1-5}$alkyl substituted with a substitutent selected from the group consisting of:
  (i) phenyl, and
  (ii) phenyl substituted with methyl, methoxy, halogen (Cl, Br, I, F) or hydroxy; and
  (iii) $C_{1-5}$ alkylcarbonyloxy;
(d) a pharmaceutically acceptable salt;

pharmaceutical compositions thereof, and their use as squalene synthetase inhibitors and their use as cholesterol lowering agents, antifungal agents and cancer treatment agents.

In one embodiment of this invention
R is

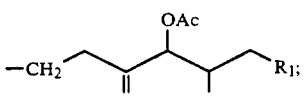

and
$R_2$ is

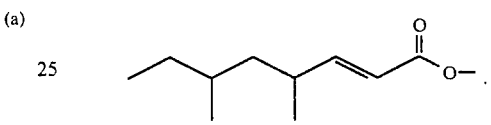

In one class of this embodiment $R_1$ is selected from

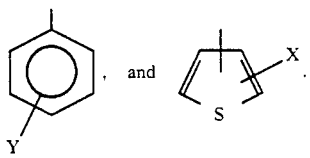

Exemplifying this class are the compounds wherein X is H and Y is F.

In a second embodiment of this invention,
R is

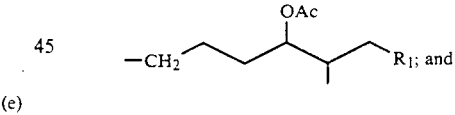

$R_2$ is

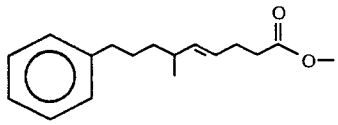

In one class of this embodiment $R_1$ is selected from:

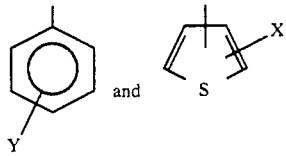

Exemplifying this class are the compounds wherein X is H and Y is F.

Compounds of formula (I) wherein R is

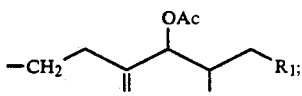

and $R_2$ is

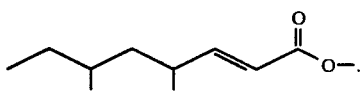

are prepared by decarboxylation at the 3-position of compounds of formula (II). Decarboxylation may be carried out by thermal or photochemical means.

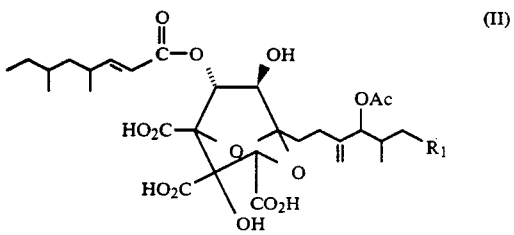

(II)

Compounds of formula (II) are prepared by a biosynthetic route which comprises the addition of a compound:

$R_1$—$CO_2H$;

wherein $R_1$ is as defined above, to a zaragozic acid A producing culture and isolating the product (II) from the culture broth.

Known zaragozic acid A producing cultures suitable for producing the compounds of formula (II) include:
(a) MF5453 (ATCC 20986),
(b) MF5565 (ATCC 74068),
(c) MF5599 (ATCC 74065),
(d) MF5572 (ATCC 74066),
(e) MF5573 (ATCC 74067).

the culture MF5453 is that of a fungus isolated from a water sample obtained from the Jalon River, Zaragoza, Spain. This culture has been deposited with the American Type Culture Collection at 12301 Parklawn Drive, Rockville, Md. 20852 as ATCC 20986. The microorganism MF5453, its morphological characteristics and a fermentation procedure using this microorganism have been described in U.S. Pat. No. 5,053,425.

The culture MF5565 is a strain of *Exserohilum rostratum*, which was isolated from bark of *Theobroma cacao* (Philippines). The culture has been deposited with the ATCC as ATCC 74068. The microorganism MF5565, its morphological characteristics and a fermentation procedure using this microorganism have been described in U.S. patent application Ser. No. 722,049 filed Jun. 27, 1992.

Strain MF5565 was recovered from the bark of *Theobroma cacao*, collected in Los Banos, Laguna Province, Philippines. Bark discs were removed with a leather punch (no. 245, C. S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar medium (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to one month for the development of fungal colonies on bark discs and the agar.

Strain MF5565 exhibits the following morphological characteristics.

Colonies relatively fast-growing, in 1 week attaining a diameter of: 50 mm on cornmeal agar (Difco Laboratories); 50–52 mm on yeast-malt extract agar (10 g malt extract, 2 g yeast extract, 20 g agar in 1 L distilled water); 60 mm on V8 juice agar (200 mL V8 juice, Campbell Soup Co., 3 g $CaCO_3$, 20 g agar diluted to 1 L distilled water). On yeast-malt agar with both submerged and aerial mucelium, with submerged mycelium sometimes forming radial strands, floccose to cottony or lanose in age, with margin appressed, minutely fimbriate to even, hyaline to pale gray at the margin but soom darkening to dark gray or dark olive-gray, or black in age, Dark Olive-Gray, Iron Gray, Dark Mouse Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions. Odors, sclerotia, stromata, or pseudothecia absent. Conidiphores arising from uppermost aerial mycelium, up to 600 μm long, 3–4.5 μm wide, straight or flexuous, with geniculate apices, with walls smooth, or occasionally finely incrusted, usually bearing 2–10 conidia, pale olive-gray to olive-gray. Conidiogenous cells polytretic, integrated, sympodial, indeterminate, terminal or intercalary, with slightly raised, darkened scars surrounding a minute pore at the conidiogenous locus. Conidia 45-250×7-20 μm, mostly 75–180 μm long, variable in shape, broadly ellipsoidal, fusoid, obclavate, or tapered cylindrical, straight to curved, or rarely sigmoid, with broadly rounded apices, smooth, 5–22 septate, with basal septum most thickened and darkened, with terminal septum often also darker than septa delimiting central cells, with a distinct cylindrical hilar appendix protruding 1–2.5 μm, pedicel-like extensions absent, initially germinating from apical and basal cells pale gray to olive-gray in 3% KOH. Hyphae septate, branched, pale olive-gray to olive-brown, usually smooth, but occasionally with fine incrustations.

Strain MF5565 belongs to the genus *Exserohilum rostratum* based on the combination of polytretic conidiogenous cells that give rise to predominately multiseptate, dematiaceous phragmoconidia. The basal cell of the conidium is delimited by a thick, darkened septum, and has a protruding hilar appendix. Strain MF5565 is identified as *Exserohilum rostratum* based on the predominance of straight and curved conidia, darkened septa delimiting both the basal and terminal cells, and relatively long conidia (A. Sivanesan. 1987 Graminicolous species of Bipolaris, Curvularia, Drechslera, Exserohilum and their telemorphs. CMI Mycological Paper No. 158).

The culture MF5599, is a strain of *Curvularia lunata* var. aeria isolated from bark of *Ficus elastica* (Diliman, Quezon City, Philippines). The culture has been deposited with the ATCC as ATCC 74065. The microorganism MF5599 has the same morphological characteristics as MF5572, described below.

The culture MF5572 is a strain of *Curvularia lunata* var. aeria, isolated from tree bark (Philippines). This culture has been deposited with the ATCC as ATCC 74066. The microorganism MF5572, its morphological characteristics and a fermentation procedure using this microorganism have been described in U.S. patent application Ser. No. 715,535 filed Jun. 14, 1991.

Strain MF5572, was recovered from the bark of an unidentified tree, collected in Diliman, Quezon City, Philippines. Bark discs were removed with a leather punch (no. 245, C.S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5572 has been identified as *Curvularia lunata* var. aeria and exhibits the following morphological characteristics.

Colonies are relatively fast-growing, in 1 week attaining a diameter of: 30–35 mm on cornmeal agar (Difco Laboratories); 30–35 mm on yeast-malt extract agar (10 g malt extract, 2 g yeast extract, 20 g agar in 1 L distilled water); 40–55 mm on V8 juice agar (200 mL V8 juice, Campbell Soup Co., 3 g $CaCO_3$, 20 g agar diluted to 1 L distilled water). On yeast-malt agar both submerged and aerial mycelia form, are slightly raised in side view, velvety to floccose when young, cottony or lanose in age, with margin slightly raised, even to wavy, hyaline to pale gray at the margin but soon darkening to grayish olive, gray, to dark olive-gray, Smoke Gray, Light Grayish Olive, Deep Olive-Gray, Dark Olive-Gray, Iron Gray, Castor Gray (capitalized color names from Ridgway, R. 1912. Color Standards and Nomenclature, Washington, D.C.), in reverse yellowish gray towards the margin but soon olivaceous gray, in age developing dark olive-black spots and patches in the agar, often with patches or tufts of hyaline to pale gray aerial hyphae developing in older portions, odors and pseudothecia absent. The surface of cultures in excess of 3 weeks old, generally develop straight to curved, cylindrical, finger-like stromata, 0.5–1 mm tall, which project upward from the oldest regions of the colony surface. Stromata formation is best on nutrient-rich media, e.g. potato-dextrose agar, oatmeal agar, or glucose-yeast-malt extract agar.

Conidiophores arising from aerial hyphae, 30–200×3–5 μm, septate, straight or flexuous, sometimes branched in age, with apices straight, curved or geniculate, smooth, thin- to slightly thick-walled, olive-brown to olive-gray in 3% KOH, bearing 2–10 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 18–28×9–14 μm, consistently 3-septate, broadly elliptical, with penultimate, distal cell curved and distinctly swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched. Stromatic tissue a textura intricata, with cells hyaline in 3% KOH.

The culture MF5573, *Curvularia lunata* var. lunata, was isolated from *Ficus elastica* tree bark (Philippines). The culture has been deposited with the ATCC as ATCC 74067. The microorganism MF5573, its morphological characteristics and a fermentation procedure using this microorganism have been described in U.S. patent application Ser. No. 715,535 filed Jun. 14, 1991.

*Curvularia lunata* var. lunata MF5573 was recovered from the bark of *Ficus elastica* collected in Diliman, Quezon City, Philippines. Bark discs were removed with a leather punch (no. 245, C. S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5573 has been identified as *Curvularia lunata* var. lunata and exhibits the following morphological characteristics.

Colonies are relatively fast-growing, in 1 week attaining a diameter of: 35–40 mm on cornmeal agar (Difco Laboratories); 40 mm on yeast-malt extract agar (10 g malt extract, 2 g yeast extract, 20 g agar in 1 L distilled water); 45–50 mm on V8 juice agar (200 mL V8 juice, Campbell Soup Co., 3 g $CaCO_3$, 20 g agar diluted to 1 L distilled water). On yeast-malt agar both submerged and aerial mycelia form, with aerial mycelia sometimes forming radial strands, floccose to cottony or lanose in age, with margin appressed, minutely fimbriate, hyaline to pale gray at the margin but soon darkening to dark gray or dark olive-gray, Castor Gray, Dark Olive-Gray, Iron Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions, occasionally forming pale gray to hyaline sectors, odors, sclerotia, stromata, or pseudothecia absent.

Conidiophores arising from surface or aerial hyphae, 15–250×3–5 μm, septate, straight or flexuous, sometimes branched in age, with apices straight, curved or geniculate, smooth, thin- to slightly thick-walled, olive-brown to olive-gray in 3% KOH, bearing 4–15 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 21–30×9–13.5 μm, usually 3-septate, infrequently 4-septate, broadly elliptical, with penultimate, distal cell curved and often obliquely swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched.

Compounds of formula (I) wherein R is

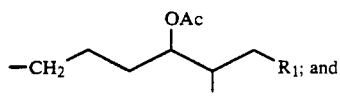

and $R_2$ is

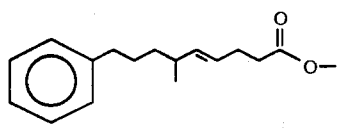

are prepared by decarboxylation at the 3-position of compounds of formula (III). Decarboxylation may be carried out by thermal or photochemical means.

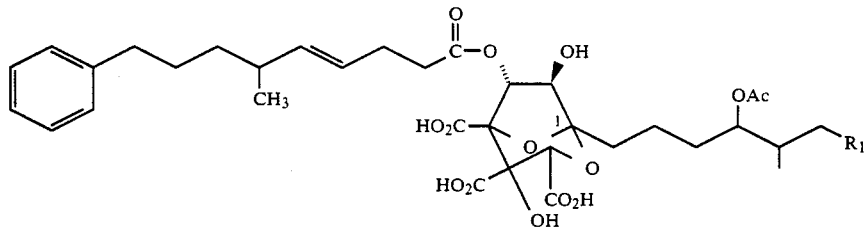

(III)

Compounds of formula (III) are prepared by a biosynthetic route which comprises the addition of a compound:

$R_1$—$CO_2H$;

wherein $R_1$ is as defined above, to a Zaragozic Acid C producing culture and isolating the product (III) from the culture broth.

Known Zaragozic Acid C producing cultures suitable for producing the compounds of formula (III) include:
(a) MF5465 (ATCC 74011),
(b) MF5701 (ATCC 74165), and
(c) MF5703 (ATCC 74166).

The compounds of formula (III) are prepared in an aerobic fermentation procedure employing strains of Leptodontium elatius. More particularly, the strains employed may be selected from strains MF5465 (ATCC 74011), MF5701 (ATCC 74165), and MF5703 (ATCC 74166), or mutants thereof. These mutants have essentially the same characteristics of the strains (i.e., MF5465 (ATCC 74011), MF5701 (ATCC 74165), and MF5703 (ATCC 74166). ) The term "mutant" refers to an MF5465 (ATCC 74011), MF5701 (ATCC 74165), or MF5703 (ATCC 74166) organism in which some gene of the genome is modified, leaving the gene or genes responsible for the organism's ability to produce a compound of formula (III) through the process of the present invention functional and heritable.

A biologically pure culture of Leptodontium elatius is defined as being originally isolated from the natural environment and free of viable contaminating microorganisms. A culture of Leptodontium elatius is defined as being originally isolated from the natural environment and free of viable contaminating microorganisms that would be deleterious to the formation of a compound of formula (III) through the process of the present invention.

The culture MF5465 is that of a fungus, a lignicolous Hyphomycete, Leptodontium elatius, isolated from wood in the Joyce Kilmer Memorial Forest in North Carolina. This culture has been deposited with the American Type Culture Collection at 12301 Parklawn Drive, Rockville, Md, 20852 as ATCC 74011 under conditions of the Budapest Treaty.

The culture MF5465, identified as Leptodontium elatius exhibits the following morphological features.

Colonies attaining 12–15 mm in 7 days on oatmeal agar (DIFCO), with both aerial and submerged mycelium. Colony surface flat to appressed in side view, minutely velvety with a metallic sheen towards the margins, dull towards the center, hyaline at the margin, but soon becoming pale to dark gray, finally black, often developing olivaceous colors in age, Pallid Neutral Gray, Light Gull Gray, Deep Gull Gray, Dark Full Gray, Slate-Gray, Deep Olive-Gray, Olive-Gray, (capitalized color names from Ridgway, R. 1912. Color Standards and Nomenclature, Washington, D.C.), with similar reverse pigmentation, without exudates diffusible pigments or odors.

Conidiogenous cells holoblastic, arising as the terminal cells of relatively undifferentiated conidiophores, with tapered, subulate apices, with the conidiogenous loci confined to the extreme apex. Occasionally with undifferentiated conidiogenous loci directly on vegetative hyphae. Developing conidia adhere to conidiophore terminus in a thin, irregular to ladder-like rachis in groups of up to 4–15 conidia. Conidiophores originating as undifferentiated branches at right or subacute angles from vegetative hyphae, gradually elongating, remaining simple or forming 1–3 branch points, usually at right to subacute angles, usually clustered in small groups when viewed from above, 1–3 septate, cylindrical to conical with tapered apices hyaline when young but developing olivaceous to olivaceous gray pigments from the base upward in age, with walls slightly thicker than those of vegetative hyphae, 20–65×3–5 μm. Conidia formed abundantly on common media such as oatmeal, malt extract, or corn meal agar, 3.5-5 μm×1-2 μm, aseptate, smooth, thin-walled, allantoid, suballantoid, to short cylindrical, or narrowly elliptical, often with a small proximal scar or apiculus, without visible slime or gelatinous materials. Hyphae septate, branched, cylindrical or occasionally inflated, up to 5 μm in diameter.

The culture MF5701 has been identified as *Leptodontium elatius* var. *elatius* and exhibits all the essential morphological characteristics of that species. It was isolated from the internal tissues of a basidioma of a wood decay basidiomycete, *Phellinus robiniae*, which was growing parasitically on *Robinia pseudoacacia* (black locust) in Sussex County, N.J. This culture has been deposited with the American Type Culture Collection at 12301 Parklawn Drive, Rockville, Md. 20852 as ATCC 74165 under conditions of the Budapest Treaty.

The culture MF5703 has been identified as *Leptodontium elatius* var. *elatius* and exhibits all the essential morphological characteristics of that species. It was isolated from wood chip mulch at Califon, N.J. (Hunterdon County). This culture has been deposited with the American Type Culture Collection at 12301 Parklawn Drive, Rockville, Md. 20852 as ATCC 74166 under conditions of the Budapest Treaty.

Strains MF5701 and MF5703 of *Leptodontium elatius* var. *elatius* exhibit the following diagnostic morphological characteristics:

Colonies 16-22 mm in diameter after two weeks on yeast-malt extract agar (YM agar, DIFCO) at 25° C., 12 hour photoperiod. Colonies raised, downy, wooly or floccose, developing suberect hyphal bundles in older portions of colonies, dull, obscurely zonate, with an even, submerged margin, hyaline at margin but soon white, pale gray, gray to dark gray in age, Pearl Gray, Pale Olive-Gray, Dawn Gray, Storm Gray, Olive-Gray (capitalized color names from Ridgway, R., *Color Standards and Nomenclature*, Washington, D.C. 1912). Reverse dull pale olivaceous yellow to grayish olive, Light Grayish Olive, Grayish Olive, Deep Grayish Olive. Odors and exudates absent.

Colonies 14-16 mm in diameter after two weeks on Emerson Yp Ss (DIFCO) agar at 25° C., 12 hour photoperiod. Colonies appressed toward margin, slightly raised toward center, obscurely radially striate, velvety, with margin even to minutely fimbriate, submerged, hyaline at margin, but soon dark olivaceous gray to olivaceous black or black, Castor Gray, Iron Gray, Olivaceous Black, Blackish Green-Gray. Reverse similar in color. Odors and exudates absent.

Colonies 18-20 mm in diameter after two weeks on corn meal agar (DIFCO) at 25° C., 12 hour photoperiod. Colonies appressed, faintly radially striate, translucent to pale translucent gray. Reverse translucent. Odors and exudates absent.

No growth occurred on yeast-malt agar after two weeks at 37° C.

Conidiophores absent or up to 100 μm tall, indeterminate, unbranched or with 1-4 simple branches from a main hyphal axis, straight or slightly geniculate, often tapering to finely pointed, geniculate apex, with wall slightly thickened at the base and becoming thinner distally, smooth-walled, septate or not, olivaceous gray to blackish gray at the base, becoming hyaline towards the apex, with a conidial rachis accumulating at the apex or occasionally with conidial adhering to intercalary regions, with conidial rachis up to 25 μm tall, with or without minute hyaline scars. Conidiogenous cells arising directly from hyphae, terminal or intercalary, holoblastic, sympodial, with conidia accumulating in a ladder-like rachis at a 90° to 45° angle with respect to main conidiophore axis, when on vegetative hyphae producing conidia in yeast-like masses. Conidia hyaline, ellipsoidal to allantoid, thin-walled, smooth, 4.5-6×1-2 μm. Vegetative hyphae septate, branched.

Vegetative cells of a culture capable of producing Zaragozic Acids, such as: MF5453 (ATCC 20986); MF5565 (ATCC 74068); MF5599 (ATCC 74065); MF5572 (ATCC 74066); MF5573 (ATCC 74067); MF5465 (ATCC 20986), MF5701 (ATCC 74165), and MF5703 (ATCC 74166); can be obtained by culturing the microorganism in an aqueous nutrient medium containing sources of assimilable carbon and nitrogen, preferably under aerobic conditions. Nutrient media may also optionally contain mineral salts, high molecular weight polyanions (CARBOPOL, JUNLON), and/or defoaming agents.

The preferred sources of carbon in the nutrient medium are carbohydrates such as glucose, glycerin, and the like. Other sources which may be included are maltose, fructose, sucrose, and the like. In addition, complex nutrient sources such as oat flour may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, and the like, as well as complex sources such as yeast extracts (hydrolysates, autolysates), dried yeast, tomato paste, peptone, corn steep liquor, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 20 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like.

The preferred process for production of these vegetative cells consists of inoculating spores or mycelia of the producing organism into a suitable medium and then cultivating under aerobic condition. The fermentation procedure generally is to first inoculate a preserved source of culture into a nutrient medium and to obtain, sometimes through a two-step process, growth of organisms which serve as seeds in the production of active compounds. After inoculation, the flasks are incubated with agitation at temperature ranging from 20° to 30° C., preferably 25° to 28° C. Agitation rates may range up to 400 rpm, preferably 200 to 220 rpm. Flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium, preferably a liquid production medium, is incubated 3 to 30 days, preferably 4 to 14 days, with or without agitation (depending on whether liquid or solid production media are employed). The fermentation is conducted aerobically at temperatures ranging from 20°–40° C. If used, agitation may be at a rate of 200 to 400 rpm. To obtain optimum results, the temperature is in the range of 22° to 28° C., most preferably 24° to 26° C. The pH of the nutrient medium suitable for the process of this invention and producing compounds of structural formula (II) or (IV) are in the range of 3.5 to 8.5, most preferably 5.0 to 7.5.

After initial incubation, the compound $R_1CO_2H$ wherein $R_1$ is as noted above is added, either as a free acid or as a biologically acceptable salt form such as sodium to a final concentration of 2 to 20 mM preferably 5 to 10 mM, and the incubation is continued for another 5 to 14 days, preferably 7 to 10 days. After the additional incubation, the biosynthesis is terminated by the addition of a solvent such as methanol or 2-butanone or by lowering the pH to about 2 by the addition of an acid such as HCl, and the compound of structural formula (II) or (III) is isolated.

After the biosynthesis is complete and the fermentation is terminated, the desired compounds of Formula (II) or (III) are extracted with solvent and purified by various chromatographic techniques such as silica gel, reverse phase and ion exchange. Preferably the compounds of Formula (II) or (III) are isolated by anion exchange chromatography followed by preparative reverse-phase high pressure liquid chromatography.

Esters of the compound of Formula (I) may be prepared by dissolving the compound of Formula (I) in a dry organic solvent, preferably tetrahydrofuran (THF) at 0°–30° C. and treating with the appropriately substituted isourea for 8-24 hours, cooling to $-15°$ C. and filtering the urea. The mono- and di- esters may be prepared by varying the number of equivalents of isourea used. The filtrate is concentrated under reduced pressure to yield the desired ester.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

In addition, the present invention is directed to a method of inhibiting the enzyme squalene synthase which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol-lowering agents such as those which inhibit another enzyme in the biosynthetic pathway in the synthesis of cholesterol. Examples of such agents would include but are not limited to HMG-CoA reductase inhibitors, HMG-CoA synthase inhibitors, and squalene epoxidase inhibitors. Illustrative of such HMG-CoA reductase inhibitors are lovastatin, simvastatin, pravastatin and fluvastatin. Examples of HMG-CoA synthase inhibitors are the beta-lactone derivatives disclosed in U.S. Pat. Nos. 4,806,564; 4,816,477; 4,847,271; and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Illustrative examples of squalene epoxidase inhibitors are disclosed in European Patent Publication EP 0 318 860 and in Japanese Patent Publication J02 169-571A. LDL-receptor gene inducer molecules are disclosed in U.S. Pat. application Ser. No. 07/670,640 filed Mar. 18, 1991. Other cholesterol lowering agents that may be administered include niacin, probucol, the fibric acids: clofibrate and gemfibrozil, and LDL-receptor gene inducers. Representative of such combinations are those containing about 10–400 mg of a compound of formula (I) in combination with about 20–100 mg of an HMG-CoA reductase inhibitor, 20 to 200 mg of a HMG-CoA synthase inhibitor, or 2 to 200 mg of a squalene epoxidase inhibitor, or 250 to 1000 mg of probucol, or 600 to 1200 mg of gemfibrozil, or 1 to 2 g of clofibrate, or 3 to 6 g of niacin, or 20 to 300 mg of an LDL-receptor gene inducer.

The compounds of this invention may also be co-administered with pharmaceutically acceptable nontoxic cationic polymers capable of binding bile acids in a non-resorbable form in the gastrointestinal tract. Examples of such polymers include cholestyramine, colestipol and poly[methyl(3-tri-methyl)aminopropyl]iminotrimethylene dihalide. The relative amounts for co-administration of the compounds of this invention and these polymers is between 1:100 and 1:15,000 (w/w).

The intrinsic squalene synthase inhibitory activity of representative compounds of this invention was measured by the standard in vitro protocol described below:

PREPARATION OF RAT LIVER MICROSOMES

CHARLES RIVER CD rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA (ethylenediaminetetraacetic acid) pH 7.5 with a Potter-Elvehjem type tissue grinder. The homogenate was centrifuged twice at 20,000×g for 15 min. at 4° C., discarding the pellet each time. The supernatant was then centrifuged at 100,000×g for 1 hr at 4° C. The resulting microsomal pellet was resuspended in a volume of the above homogenizing buffer equal to one-fifth the volume of the original homogenate. This microsomal preparation has a protein concentration of about 7 mg/mL. The microsomal suspensions were stored in aliquots at −70° C. Squalene synthase activity in these aliquots is stable for at least several months.

Squalene Synthase Assay

Reactions were performed in 13×100 mm test tubes. If the squalene epoxidase inhibitor is not used, the assay must be performed under anaerobic conditions, and screw top test tubes are used. A batch assay mix was prepared from the following solution:

| | μL per assay |
|---|---|
| 1. 250 mM HEPES pH 7.5 | 20 |
| 2. KF or NaF 110 mM | 10 |
| 3. $MgCl_2$ 55 mM | 10 |
| 4. Dithiothreitol 30 mM | 10 |
| 5. NADPH 10 mM (made fresh) | 10 |
| 6. [$^3$H]farnesyl-pyrophosphate 15 Ci/mmole, 33 μM | 1.0 |
| 7. squalene epoxidase inhibitor such as Banyu FW-439H (optional)(50 μg/mL) | 2 |
| 8. $H_2O$ | 25 |

If a squalene epoxidase inhibitor (ingredient (7) above), such as Banyu's FW-439H, is not used, the assay mix is degassed under a vacuum and flushed with $N_2$. Solutions of the squalene synthase inhibitors were prepared either in DMSO or MeOH and a 1:120 or so as needed dilution of the microsomal protein was made with the original homogenizing buffer. For each reaction, 88 μL of the assay mix was taken with 2 μL of an inhibitor solution (DMSO or MeOH in the controls), warmed to 30° C. in a water bath and then the reaction was initiated by the addition of 10 μL of the 1:120 dilution of microsomal protein (0.6 μg protein total in the assay). The reactions were stopped after 20 minutes by the addition of 100 μL of a 1:1 mix of 40% KOH with 95% EtOH, and cooled. Two mL of heptane was added and the mix was vortexed. Activated alumina (0.5 g) was then added, the mix vortexed again, the alumina allowed to settle and some volume (about 0.7 mL) of the heptane layer was removed. Five mL of scintillation fluid was added to the heptane solution and radioactivity was determined by liquid scintillation counting.

Percent inhibition is calculated by the formula:

$$1 - \frac{[Sample - Blank]}{[Control - Blank]} \times 100$$

The present compounds also demonstrate broad spectrum antifungal activity. Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

Furthermore, the compounds of the present invention inhibit farnesyl-protein transferase and thereby inhibit the farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (FTase) from bovine brain is chromatographed on DEAE-Sephacel (PHARMACIA, 0–0.8M NaCl gradient elution), N-octyl agarose (SIGMA, 0–0.6M NaCl gradient elution), and a MONO Q HPLC column (PHARMACIA, 0–0.3M NaCl gradient). Ras-CVLS at 3.5 μM, 0.25 μM [$^3$H]FPP, and the indicated compounds are incubated with this partially purified enzyme preparation.

RASIT ASSAY II

Farnesyl-protein transferase (FTase) from bovine brain was chromatographed on DEAE-Sephacel (PHARMACIA, 0–0.8M NaCl gradient elution), N-octyl agarose (SIGMA, 0–0.6M NaCl gradient elution), and a MONO Q HPLC column (PHARMACIA, 0–0.3M NaCl gradient). Ras-CVLS at 1.0 μM, 0.5 μM [$^3$H]FPP, and the indicated compounds are incubated with this partially purified enzyme preparation. The FTase data is a measurement of the ability of the test compound to inhibit Ras farnesylation in vitro.

The pharmaceutical compositions containing the compounds of structural Formula (I) inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably between 0.5 mg/kg of body weight to about 10 mg/kg of body weight of a mammal a day.

The following examples illustrate the formation of a compound of formula (I).

EXAMPLE 1

A Compound of Formula (I) wherein R is

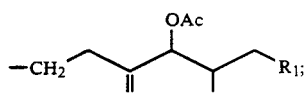

and $R_2$ is

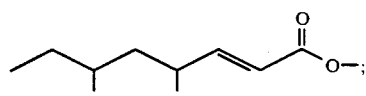

and $R_1$ is 2-thiophene (IA).

I. Directed Biosynthesis: Preparation of a compound of formula (II) wherein $R_1$ is 2-thiophene (IIA)

Culture MF5453 was grown for 72 hours at 25° C. in KF medium (U.S. Pat. No. 5,053,425) and the cells harvested by centrifugation. The cells were washed (×2) with distilled water and resuspended to the original broth volume in 20 mM piperazine-N,N'-bis[2-ethanesulfonic acid] (PIPES) buffer (pH 6.1) containing 3% sucrose. Five mL aliquots of this suspension were transferred to each of four 50 mL Erlenmeyer flasks and these flasks incubated at 25° C. with agitation. After 24 hours incubation, 2-thiophene-carboxylic acid (Na-salt) was added to a final concentration of 0.25 mM, 0.5 mM and 1.0 mM to each of three of the flasks respectively, and the fourth remained a control. After an additional 96 hours incubation the biosynthesis was terminated with the addition of two volumes of methanol and the broths clarified. The broth-methanol mixture was adjusted to pH 4.5 with formic acid. The contents of the three flasks to which the 2-thiophene carboxylic acid had been added were combined. The resulting mixture was applied to a 1 mL column of BIO-RAD ® AG4X4 ion exchange resin in the formate cycle. The column was washed successively with 15 mL of MeOH-formate buffer (1/1 v/v; 50 mM formate adjusted to pH 4.5) and 15 mL of 60/40 MeCN/water (v/v). The column was then eluted with 15 mL of 60/40 MeCN/water containing 1 mL concentrated formic acid.

II. Isolation and Purification:

Fifteen mL of AG4X4 eluate was reduced under nitrogen to 8 mL. The crude extract was filtered and 2 mL injected onto a BECKMAN ® preparative HPLC (9.6 mm×250 mm) ODS column. The column was developed at 3.0 mL/min using a 35 minute linear gradient of 40% to 80% acetonitrile in water containing 0.1% $H_3PO_4$. Detection was at 215 nm. Peaks with an elution time of 28.9 minutes were collected and pooled. The pooled material was diluted with four volumes of deionized water and applied to a water-equilibrated $C_{18}$ SPE column. After washing with five volumes of deionized water, the column was dried with nitrogen, then eluted with methanol. The eluate was evaporated to dryness to yield the compound (IIA).

$^1$H NMR (CD$_3$OD): 7.155 (dd, J=5.0, 1.2, 1H) 6.90 (dd, J=5.1, 3.4, H) 6.84 (dd, J=15.7, 8.5, 1H) 6.83 (dq, J=35, 1.0, 1.0, 1.0, 1H) 6.30 (d, 1.9, 1H) 5.80 (dd, 15.7, 1.0, 1H) 5.26 (s, 1H) 5.12 (d, 4.6, 1H) 5.02 (s, 1H) 4.96 (s, 1H) 4.05 (d, 1.7, 1H) 2.88 (dd, 14.8, 7.0, 1H) 2.71 (dd, 14.8, 8.1, 1H) 2.44 (m, 2H), 2.31 (m, 1H), 2.24 (m, 1H) 2.09 (s, 3H) 2.05 (m, 2H) 1.27–1.42 (m, 4H) 1.09–1.20 (m, 2H) 1.03 (d, 3H) 0.93 (d, 3H) 0.86 (t, 3H) 0.85 (d, 3H)

III. Decarboxylation i) Preparation of IIA-3-benzyl ester (1)

A solution of acetyl chloride (0.4 ml) in benzyl alcohol (10 ml) is stirred at room temperature for 30 min. To this mixture is added compound IIA from step II (1 g) and the reaction mixture is stirred for an additional 6 hr. The mixture is poured into acetonitrile-water (200 mL, 38%) and purified by chromatography (C-8, acetonitrile-water, 3:2) to give the title compound (1).

ii) Preparation of IIA-3-benzyl-4,5-t-butyl ester (2)

To a solution of (1) (100 mg) in methylene chloride (2 mL) is added O-t-butyl-N,N'-diisopropylisourea (300 mg) and the solution is stirred at 40° C. for 2 days. The reaction mixture is then cooled to room temperature, concentrated in vacuo and filtered through silica eluting with ethyl acetate:hexane, 1:4 to yield the title compound (2).

iii) Preparation of IIA-4,5-t-butyl ester (3)

To a solution of compound (2) (100 mg) in methanol (4 mL) is added 1-methyl-1,4-cyclohexadiene (200 uL) and Pd/C (50 mg). The reaction mixture is stirred at 30°–35° C. for 1.5 hr and filtered over celite. The filtrate is evaporated in vacuo to give the title compound (3).

iv) Preparation of IIA-3-phenylselenoester-4,5-di-t-butyl ester (4)

To a room temperature solution of compound (3) in THF (160 mL) is added triethylamine (3.35 mL, 24.09 mmol) followed by dichlorophenyl phosphate (2.34 mL, 15.65 mmol). The reaction is allowed to stir until TLC indicated complete disappearance of the starting material. Upon complete consumption of the starting material triethylamine (3.35 mL, 24.1 mmol) is added followed by phenyl selenol (1.92 mL, 18.06 mmol). The reaction is allowed to stir at room temperature overnight whereupon it is diluted with EtOAc washed with water, salt, saturated sodium bicarbonate, brine, dried (MgSO$_4$) and concentrated. Chromatography of the residue (silica gel, 9:1 to 4:1 to 2:1 hexanes:EtOAc) gives the selenoester (4).

v) Preparation of IA-4,5-di-t-butyl ester (5)

To an 80° C. solution of n-Bu$_3$Sn-H (0.17 mL, 0.64 mmol) and AIBN (15 mg) in benzene (1.0 mL) is added the seleno ester (4) (0.20 g, 0.21 mmol) dropwise. The reaction is allowed to stir until TLC indicated complete disappearance of the starting material. Upon complete consumption of the starting material the reaction is concentrated in vacuo and the residue is chromatographed (silica gel, 3:1 hexanes:EtOAc) to give the decarboxylated material. (5)

vi) Preparation of IA

To an ambient solution of compound (5) (1.6 g) in CH$_2$Cl$_2$ (30 mL) is added TFA (10 mL). The reaction is allowed to stir overnight whereupon it is concentrated in vacuo. The residue is azeotropically dried with toluene (3×5 mL) and lyophilized from benzene to yield compound (IA).

EXAMPLE 2

Preparation of IA-4-methylpivalate ester (6)

To a solution of IA (197.6 mg, 0.31 mmol) in refluxing acetonitrile (3.0 mL), is added DBU (0.33 mmol, 49.0 ul) followed by chloromethyl pivalate (0.61 mmol, 82.0 ul) and a few crystals of sodium iodide. The reaction is allowed to stir overnight whereupon it is concentrated in vacuo and the residue purified by preparative HPLC, using a C-8 reverse phase column and a gradient solvent mixture 60% H$_2$O/40% acetonitrile to 100% acetonitrile over 40 minutes with a flow rate of 10 mL/min, to yield the C-4 POM ester. (6)

EXAMPLE 3

Preparation of a Compound of Formula I wherein R is

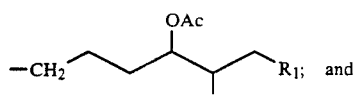

and R$_2$ is

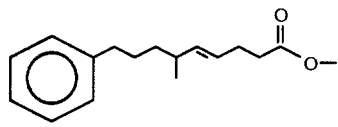

and R$_1$ is 2-thiophene (IB).

I. Directed Biosynthesis: Preparation of a compound of formula (III) wherein R$_1$ is 2-thiophene (IIIB)

A frozen vegetative mycelia of MF5465, *Leptodontium elatius* (ATCC 74011) was used to inoculate a starch seed flask (40 mL per 250 mL Erlenmeyer), then incubated at 25° C. for 48 h. One mL of this seed was used to inoculate a 1.5×modified GPT medium production flask (40 mL per 250 mL Erlenmeyer).

| Starch Seed Medium | g/L | 1.5 × modified GPT Medium | g/L |
|---|---|---|---|
| starch (AMIDEX) | 30.0 | Peptone (PRIMATONE) | 22.5 |
| Cottonseed flour (PHARMAMEDIA) | 10.0 | Glycerol | 100.0 |
| KH$_2$PO$_4$ | 9.0 | Yeast Extract (DIFCO) | 7.5 |
| Yeast Extract (FIDCO) | 5.0 | Sodium Citrate | 11.0 |
| Cerelose | 10.0 | Lactose | 50.0 |
| MgSO$_4$.7H$_2$O | 0.2 | MgSO$_4$.7H$_2$O | 0.5 |
| Adj. pH to 6.0 | | Adj. pH to 6.0 | |

The production flasks were incubated at 25° C. with agitation (220 rpm) for fourteen days, followed by addition of 2-thiophene carboxylic acid (1.25 mg/mL) and continued incubation for seven additional days. The fermentation was terminated by adjusting the whole broth pH to 2.0 and extracting with methylethyl ketone (MEK). The MEK extracts were evaporated to dryness.

II. Isolation and Purification:

Extracts from two production flasks were dissolved in twenty mL of 60% MeCN in water and insoluble material filtered. A two mL sample was injected onto an Beckman Ultrasphere ODS column (10 mm×250 mm). The column was developed at 3.0 mL/min using a gradient from 40% to 85% MeCN in HPLC-grade water containing 0.1% phosphoric acid (v/v) over a forty-two minute period. Detection was at 205 nm. A peak eluting at 33 minutes was collected. The peak fraction was diluted with an equal volume of distilled water, then applied to a water equilibrated C$_{18}$ SPE column. After washing with distilled water, the column was dried with nitrogen, then eluted with acetonitrile. The eluate was evaporated to dryness to yield a substance identified as the title compound. The $^1$H NMR 400 MHz (CD$_3$OD) of the title compound (IIIB) exhibits the following characteristic resonances:

7.22 (t, 2H), 7.13 (m, 4H), 6.88 (dd, J=5.1, 3.4, 1H), 6.79 (dd, J=3.3, ca 1, 1H), 6.23 (d, J=ca 1.5, 1H), 5.38 (dt, J=15.4, 5.9, 1H), 5.32 (dd, J=15.4, 7.5, 1H), 5.16 (s, 1H), ca 4.9 (m, 1H), 3.95 (d, J=1.7, 1H), 2.90 (dd, J=14.4, 6.1, 1H), 2.63 (dd, J=14.4, 8.6, 1H), 2.56 (m, 2H) 2.34 (m, 2H), 2.27 (m, 2H), 2.08 (m, 1H), 2.05 (s, 3H), 2.03 (m, 1H), 1.87 (m, 2H), 1.52–1.69 (m, approx. 6H), 1.24–1.34 (m, approx. 3H), 0.93 (d, J=6.8, 6H).

III. Decarboxylation i) Preparation of IIIB-3-benzyl ester (7)

A solution of acetyl chloride (0.4 ml) in benzyl alcohol (10 mL) is stirred at room temperature for 30 min. To this mixture is added compound IIB from step II (1 g) and the reaction mixture is stirred for an additional 6 hr. The mixture is poured into acetonitrile-water (200 mL, 38%) and purified by chromatography (C-8, acetonitrile-water, 3:2) to give the title compound (7).

ii) Preparation of IIIB-3-benzyl-4,5-t-butyl ester (8)

To a solution of (7) (100 mg) in methylene chloride (2 mL) is added O-t-butyl-N,N'-diisopropylisourea (300 mg) and the solution is stirred at 40° C. for 2 days. The reaction mixture is then cooled to room temperature, concentrated in vacuo and filtered through silica eluting with ethyl acetate:hexane, 1:4 to yield the title compound (8).

iii) Preparation of IIIB-4,5-t-butyl ester (9)

To a solution of compound (8) (100 mg) in methanol (4 mL) is added 1-methyl-1,4-cyclohexadiene (200 uL) and Pd/C (50 mg). The reaction mixture is stirred at 30°–35° C. for 1.5 hr and filtered over celite. The filtrate is evaporated in vacuo to give the title compound (9).

iv) Preparation of IIIB-3-phenylselenoester-4,5-di-t-butyl ester (10)

To a room temperature solution of compound (9) in THF (160 mL) is added triethylamine (3.35 mL, 24.09 mmol) followed by dichlorophenyl phosphate (2.34 mL, 15.65 mmol). The reaction is allowed to stir until TLC indicated complete disappearance of the starting material. Upon complete consumption of the starting material, triethylamine (3.35 mL, 24.1 mmol) is added followed by phenyl selenol (1.92 mL, 18.06 mmol). The reaction is allowed to stir at room temperature overnight whereupon it is diluted with EtOAc, washed with water, salt, saturated sodium bicarbonate, brine, dried (MgSO$_4$) and concentrated. Chromatography of the residue (silica gel, 9:1 to 4:1 to 2:1 hexanes:EtOAc) gives the selenoester (10).

v) Preparation of IB-4,5-di-t-butyl ester (11)

To an 80° C. solution of n-Bu$_3$Sn-H (0.17 mL, 0.64 mmol) and AIBN (15 mg) in benzene (1.0 mL) is added the seleno ester (10) (0.20 g, 0.21 mmol) dropwise. The reaction is allowed to stir until TLC indicated complete disappearance of the starting material. Upon complete consumption of the starting material the reaction is concentrated in vacuo and the residue is chromatographed (silica gel, 3:1 hexanes:EtOAc) to give the decarboxylated material. (11)

vi) Preparation of IB

To an ambient solution of compound (11) (1.6 g) in $CH_2Cl_2$ (30 mL) is added TFA (10 mL). The reaction is allowed to stir overnight whereupon it is concentrated in vacuo. The residue is azeotropically dried with toluene (3×5 mL) and lyophilized from benzene to yield compound (IB).

EXAMPLE 4

Preparation of IB-4-methylpivalate ester (12)

To a solution of IB (197.6 mg, 0.31 mmol) in refluxing acetonitrile (3.0 mL), is added DBU (0.33 mmol, 49.0 ul) followed by chloromethyl pivalate (0.61 mmole, 82.0 ul) and a few crystals of sodium iodide. The reaction is allowed to stir overnight whereupon it is concentrated in vacuo and the residue purified by preparative HPLC, using a C-8 reverse phase column and a gradient solvent mixture 60% $H_2O$/40% acetonitrile to 100% acetonitrile over 40 minutes with a flow rate of 10 ml/min, to yield the C-4 POM ester. (12)

EXAMPLE 5

Preparation of an Ammonium Salt

A 0.1 mmol sample of the free acid of a compound of formula (I) is dissolved in 10 mL ethyl acetate. The resulting solution is saturated with gaseous ammonia and the ammonium salt precipitates from solution.

EXAMPLE 6

Preparation of a Potassium Salt

A solution of 0.1 mmol of the free acid of a compound of formula (I) in 10 mL methanol is treated with an aqueous or methanolic solution containing 0.2 mmol of potassium hydroxide. Evaporation of the solvent affords the tri-potassium salt. Addition of between 0.1 and 0.2 mmol of potassium hydroxide yields analogously mixtures of the mono-potassium and di-potassium salts whose composition depends upon the exact amount of potassium hydroxide added.

In a similar fashion, the sodium and lithium salts can be formed.

EXAMPLE 7

Preparation of a Calcium Salt

A solution of 0.1 mmol of the free acid of a compound of formula (I) in 20 mL 6:4 methanol:water is treated with an aqueous solution of 0.1 mmol of calcium hydroxide. The solvents are evaporated to give the corresponding calcium salt.

EXAMPLE 8

Preparation of an Ethylenediamine Salt

A solution of 0.1 mmol of the free acid of a compound of formula (I) in 10 mL of methanol is treated with 0.1 mmol of ethylenediamine. Evaporation of the solvent affords the ethylenediamine salt. The procedure can also be applied to the preparation of the N,N''-dibenzylethylenediamine salt.

EXAMPLE 9

Preparation of a Tris(hydroxymethyl)aminomethane Salt

To a solution of 0.1 mmol of the free acid of a compound of formula (I) in 10 mL of methanol is added from 0.1 to 0.2 mmol of tris(hydroxymethyl) aminomethane dissolved in 10 mL of methanol. Evaporation of the solvent gives a corresponding salt form, the exact composition of which is determined by the molar ratio of amine added. Similarly prepared are the salts of L-ornithine, L-lysine, and N-methylglutamine.

EXAMPLE 10

Preparation of an L-arginine Salt

A solution of 0.1 mmol of the free acid of a compound of formula (I) in 20 mL of 6:4 methanol:water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglutamine.

EXAMPLE 11

Preparation of a the dimethyl ester of a Compound of Formula (I) (Method I)

To 5 mg of the free acid of a compound of formula (I) in methanol (5 mL) is added 2 mL of freshly distilled diazomethane in ether (2.05M). After 5 minutes the solvent is removed to afford dimethyl ester as an oil.

EXAMPLE 12

Preparation of a the dimethyl ester of a Compound of Formula (I) (Method II)

To 0.6 mg of the free acid of a compound of formula (I) in 1 mL diethyl ether at 0° C. is added etheral cyanamide dropwise until the solution remains yellow. The solution is evaporated under a stream of nitrogen to yield the dimethyl ester.

EXAMPLE 13

Preparation of the dibenzyl ester of a Compound of Formula (I)

To a solution of 5 mg of the free acid of a compound of formula (I) in 0.5 mL tetrahydrofuran (THF) is treated at room temperature with 2 equivalents of N,N'-diisopropyl-O-benzyl isourea for 18 hours. The reaction mixture is then chilled to −15° C., and filtered to remove the urea. The filtrate is concentrated under reduced pressure to yield the dibenzyl ester.

The method of Example 13 is also suitable for the preparation of other ester derivatives such as 1) ethyl and the other lower alkyls, and 2) substituted benzyl esters, using the appropriately substituted isourea. By varying the number of equivalents of the substituted isourea used, the mono-, di-, and tri-substituted esters may be selectively prepared.

EXAMPLE 14

Preparation of a Pivaloyl ester of a compound of Formula (I)

To a solution of the free acid of a compound of Formula (I) in refluxing acetonitrile, 2 equivalents of DBU (1,8-diazabicyclo[5.4.0] undec-7-ene) and 2 equivalents of chloromethyl pivalate are added and refluxed till completion of reaction. The product di-acid is purified by reverse phase HPLC (reverse phase column, eluted with acetonitrile-water).

The method of Example 14 is also suitable for the preparation of other ester derivatives such as 1) $C_{1-5}$ alkylcarbonyloxy$C_{1-5}$ alkyl, and 2) $C_{1-5}$ alkoxycarbonyloxy$C_{1-5}$ alkyl, using the appropriately substituted halide. By varying the number of equivalents of the substituted halide and DBU used, the mono- and di-substituted esters may be selectively prepared.

EXAMPLE 15

Oral Composition

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

What is claimed is:

1. A compound of structural formula (I)

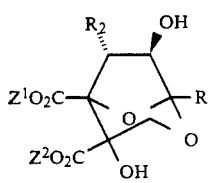

(I)

wherein

R is selected from the group consisting of

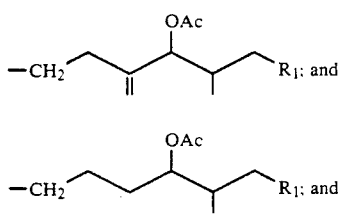

a)

b)

$R_2$ is selected from the group consisting of

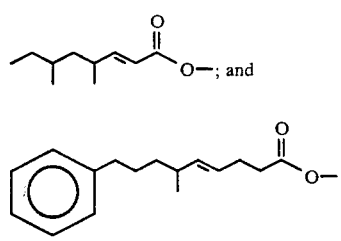

a)

b)

provided that when R is

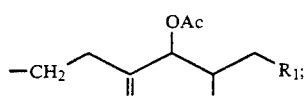

a)

then $R_2$ is

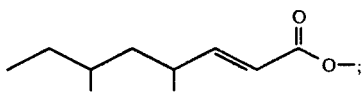

a)

and when R is

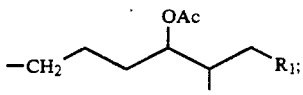

then $R_2$ is

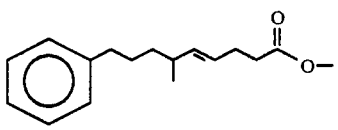

and $R_1$ is selected from the group consisting of:

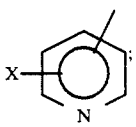

(a)

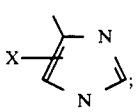

(b)

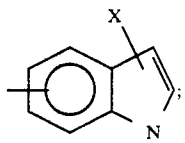

(c)

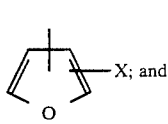

(d)

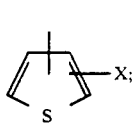

(e)

wherein X is selected from the group consisting of:
(a) H;
(b) halogen (F, Cl, Br, I);
(c) OH; and
(d) $CH_3$;

and wherein $Z^1$ and $Z^2$, are each independently selected from the group consisting of
(a) H;
(b) $C_{1-5}$ alkyl;
(c) $C_{1-5}$ alkyl substituted with a substituent selected from the group consisting of:
 (i) phenyl,
 (ii) phenyl substituted with methyl, methoxy, halogen (Cl, Br, I, F) or hydroxy; and
 (iii) $C_{1-5}$ alkylcarbonyloxy;

or a pharmaceutically acceptable salt.

2. A compound of claim 1 wherein

R is
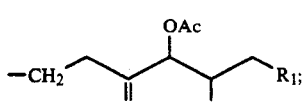
and
R₂ is
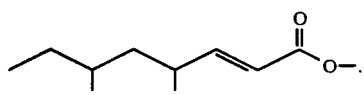
3. A compound of claim 2 wherein R₁ is
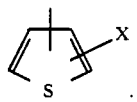
4. A compound of claim 3 wherein X is H.
5. A compound of claim 1 wherein
R is
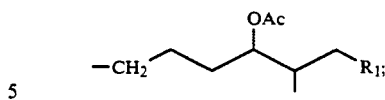
and R₂ is
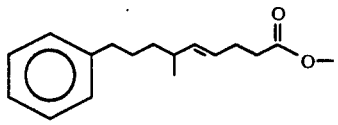
6. A compound of claim 5 wherein R₁ is
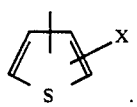
7. A compound of claim 6 wherein X is H.
8. The compound of claim 7 wherein
R₁ is
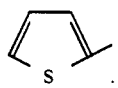
* * * * *